US012753394B2

(12) United States Patent
Kim et al.

(10) Patent No.: US 12,753,394 B2

(45) Date of Patent: Oct. 6, 2026

(54) COMPOSITION FOR ENHANCING REPROGRAMMING EFFICIENCY FROM SOMATIC CELL TO INDUCED PLURIPOTENT STEM CELL, COMPRISING mTOR ACTIVATOR, AND METHOD FOR ENHANCING REPROGRAMMING EFFICIENCY BY USING SAME

(71) Applicant: KOREA UNIVERSITY RESEARCH AND BUSINESS FOUNDATION, Seoul (KR)

(72) Inventors: Byung Soo Kim, Seoul (KR); Seung Jin Lee, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 1019 days.

(21) Appl. No.: 17/780,656

(22) PCT Filed: Nov. 27, 2020

(86) PCT No.: PCT/KR2020/017172

§ 371 (c)(1), (2) Date: May 27, 2022

(87) PCT Pub. No.: WO2021/107715

PCT Pub. Date: Jun. 3, 2021

(65) Prior Publication Data

US 2023/0013363 A1 Jan. 19, 2023

(30) Foreign Application Priority Data

Nov. 29, 2019 (KR) ........................ 10-2019-0157361

(51) Int. Cl.
*C12N 5/074* (2010.01)

(52) U.S. Cl.
CPC ........ *C12N 5/0696* (2013.01); *C12N 2500/84* (2013.01); *C12N 2501/21* (2013.01); *C12N 2501/602* (2013.01); *C12N 2501/603* (2013.01); *C12N 2501/604* (2013.01); *C12N 2501/606* (2013.01); *C12N 2501/727* (2013.01); *C12N 2501/999* (2013.01); *C12N 2506/025* (2013.01); *C12N 2506/1307* (2013.01)

(58) Field of Classification Search
CPC .............. C12N 5/0696; C12N 2500/84; C12N 2501/21; C12N 2501/602; C12N 2501/603; C12N 2501/604; C12N 2501/606; C12N 2501/727; C12N 2501/999; C12N 2506/025; C12N 2506/1307

See application file for complete search history.

(56) References Cited

U.S. PATENT DOCUMENTS

| | | | | |
|---|---|---|---|---|
| 2012/0264215 A1* | 10/2012 | Kim | C12N 5/0606 | 435/405 |
| 2013/0267030 A1* | 10/2013 | Yamanaka | C12N 5/0696 | 435/325 |
| 2019/0367871 A1* | 12/2019 | Benvenisty | C12N 15/11 | |

FOREIGN PATENT DOCUMENTS

| | | | |
|---|---|---|---|
| JP | 2016-502839 | A | 2/2016 |
| JP | 2019-527068 | A | 9/2019 |
| KR | 10-2019-0076692 | A | 7/2019 |
| KR | 10-2019-0115394 | A | 10/2019 |
| WO | WO-2012/074117 | A1 | 6/2012 |

OTHER PUBLICATIONS

Duan et al (Front. Neurosci. 13:867. doi: 10.3389/fnins.2019.00867, Sep. 4, 2019). (Year: 2019).*

Office Action from corresponding Japanese Patent Application No. 2022-532143, dated May 30, 2023.

Huangfu, D., et al.; "Induction of pluripotent stem cells by defined factors is greatly improved by small molecule compounds", Nat. Biotechnol., 2008 , vol. 26, No. 7,pp. 795-797.

Duan, Q., et al.; "Valproic Acid Enhances Reprogramming Efficiency and Neuronal Differentiation on Small Molecules Staged-Induction Neural Stem Cells; Suggested Role of mTOR Signaling", Frontiers in Neuroscience, 2019, vol. 13, Article 867, inner pp. 1-14.

Jung, J., et al.; "CXCR2 Inhibition in Human Pluripotent Stem Cells Induces Predominant Differentiation to Mesoderm and Endoderm Through Repression of mTOR, β-Cateninm, and hTERT Activities", Stem Cells Development, 2016, vol. 13, pp. 1006-1019.

Choi, Y. J, et al.; "Inhibitory effect of mTOR activator MHY1485 on autophagy: suppression of lysosomal fusion" PLOS One, 2012, vol. 7, No. 8, e43418, inner pp. 1-10.

Gao, S., et al.; "mTOR Regulates the Proliferation and Differentiation of Tendon Stem Cells: An in Vitro Study", Journal of Aging Research & Lifestyle, 2017, vol. 6, pp. 168-175.

Wang, S. ,et al.; "Transient activation of autophagy via Sox2-mediated suppression of mTOR is an important early step in reprogramming to pluripotency", Cell Stem Cell, 2013, vol. 13, No. 5, pp. 617-625.

Lee, S., et al.; "CXCR2 Ligands and mTOR Activation Enhance Reprogramming of Human Somatic Cells to Pluripotent Stem Cells", Stem Cells and Development, 2020, vol. 29, No. 3, pp. 119-132.

(Continued)

*Primary Examiner* — Peter Paras, Jr.
*Assistant Examiner* — Khoa Nhat Tran
(74) *Attorney, Agent, or Firm* — Harness, Dickey & Pierce, P.L.C.

(57) ABSTRACT

The present invention relates to a composition for enhancing reprogramming efficiency from somatic cells to induced pluripotent stem cells, comprising an mTOR activator, and a method for enhancing reprogramming efficiency by using same. In the method, reprogramming factors including OCT4, SOX2, c-Myc, and KLF4 are transduced into somatic cells, followed by treatment with an mTOR activator, thereby remarkably increasing reprogramming efficiency into induced pluripotent stem cells. Therefore, the composition and method can be used for effectively inducing the reprograming of somatic cells into induced pluripotent stem cells.

4 Claims, 7 Drawing Sheets

(56) References Cited

OTHER PUBLICATIONS

Lee, S,; "CVCR2 activation promotes the production of induced Pluripotent Stem Cells", Ph.D. thesis, Korea University, Feb. 2020.
International Search Report from corresponding PCT Application No. PCT/KR2020/017172, dated Mar. 12, 2021.

* cited by examiner

COMPOSITION FOR ENHANCING REPROGRAMMING EFFICIENCY FROM SOMATIC CELL TO INDUCED PLURIPOTENT STEM CELL, COMPRISING mTOR ACTIVATOR, AND METHOD FOR ENHANCING REPROGRAMMING EFFICIENCY BY USING SAME

CROSS-REFERENCE TO RELATED APPLICATIONS

This application is a national phase application of PCT Application No. PCT/KR2020/017172, filed on Nov. 27, 2020, which claims the benefit and priority to Korean Patent Application No. 10-2019-0157361, filed on Nov. 29, 2019. The entire disclosures of the applications identified in this paragraph are incorporated herein by references.

TECHNICAL FIELD

The present disclosure relates to a composition comprising a mammalian target of rapamycin (mTOR) activator for enhancing reprogramming efficiency from somatic cells to induced pluripotent stem cells and a method for enhancing reprogramming efficiency by using same. More specifically, the present disclosure relates to a method for increasing reprogramming efficiency to induced pluripotent stem cells wherein reprogramming factors including OCT4, SOX2, c-Myc, and KLF4 are transduced into somatic cells, followed by treatment of the somatic cells with MHY1485 (4,6-di-4-morpholinyl-N-(4-nitrophenyl)-1,3,5-triazin-2-amine).

BACKGROUND ART

Indispensable for the production of stem cell therapy products is in-vitro mass culture of stem cells, which are the sources thereof. For use in clinical applications, stem cell therapy products must also be safe and economically advantageous. However, current culturing methods of proliferating human pluripotent stem cells employ animal-derived feeder cells or are carried out in a vessel coated with a special gel including an animal-derived product, which is prone to contamination with xenoproteins, giving rise to concerns with safety. In addition, proliferative culturing methods employing expensive special gels are not suitable for mass production in terms of economic aspect.

mTOR is known to have an influence on dedifferentiation from somatic cells to induced pluripotent stem cells according to various conditions and modes including doses, treatment time, whether mTOR is regulated or activated, etc. In a conventional concept, for example, macroautophagy that occurs before introduction of a reprogramming factor into somatic cells involves an intracellular rearrangement whereby the ATP saved with the subsequent decrease of cellular respiration can be utilized to induce reprogramming.

However, the conditions under which the reprogramming is inhibited or activated are not yet clearly defined.

SUMMARY

Technical Problem

Research conducted by the present inventors resulted in the finding that the reprogramming efficiency from somatic cells to induced pluripotent stem cells (iPSCs) is remarkably increased when reprogramming factors including OCT4, SOX2, c-Myc, and KLF4 are transduced into the somatic cells, followed by treatment with an mTOR activator.

Accordingly, an aspect of the present disclosure is to provide a composition comprising an mTOR activator for enhancing reprogramming efficiency from somatic cells to induced pluripotent stem cells.

Another aspect of the present disclosure is to provide a method for enhancing reprogramming efficiency from somatic cells to induced pluripotent stem cells, the method comprising a step of incubating somatic cells with an mTOR activator.

A further aspect of the present disclosure is to provide a use of an mTOR activator for enhancing reprogramming efficiency from somatic cells to induced pluripotent stem cells.

Solution to Problem

The present disclosure relates to a composition comprising an mTOR activator for enhancing reprogramming efficiency from somatic cells to induced pluripotent stem cells (iPSCs), and a method for enhancing reprogramming efficiency by using same.

The present inventors found that treatment with the mTOR activator 4,6-di-4-morpholinyl-N-(4-nitrophenyl)-1,3,5-triazin-2-amine subsequent to the transduction of the reprogramming factors including OCT4, SOX2, c-Myc, and KLF4 to the somatic cells remarkably increased reprogramming efficiency to induced pluripotent stem cells.

Below, a detailed description will be given of the present disclosure.

Provided according to an aspect of the present disclosure is a composition containing an mTOR activator for enhancing reprogramming efficiency from somatic cells to induced pluripotent stem cells.

In an embodiment of the present disclosure, the mTOR activator may be 4,6-di-4-morpholinyl-N-(4-nitrophenyl)-1,3,5-triazin-2-amine or a derivative thereof, but with no limitations thereto.

As used herein, the term "mTOR activator" refers to a substance that activates mTOR in a reprogramming mechanism after introduction of a reprogramming factor. Through the mechanism of activating mTOR, the mTOR activator upregulates the expression of CXCR2 and cMYC and decreases autophagy activity. With the mechanism, the mTOR activator exhibits an effect of enhancing reprogramming efficiency. Therefore, so long as it activates mTOR in a reprograming mechanism subsequent to the introduction of a reprogramming factor, any mTOR activator may be used without limitations.

In an embodiment of the present disclosure, MHY1485 is used at a concentration of 0.1 to 10.0 μg/mL, 0.2 to 10.0 μg/mL, 0.5 to 10.0 μg/mL, 0.8 to 10.0 μg/mL, 0.1 to 5.0 μg/mL, 0.2 to 5.0 μg/mL, 0.5 to 5.0 μg/mL, 0.8 to 5.0 μg/mL, 0.1 to 5.0 μg/mL, 0.2 to 5.0 μg/mL, 0.5 to 5.0 μg/mL, 0.8 to 5.0 μg/mL, 0.8 to 3.0 μg/mL, 0.1 to 3.0 μg/mL, 0.2 to 3.0 μg/mL, 0.5 to 3.0 μg/mL, or 0.8 to 3.0 μg/mL, for example, 1.0 to 3.0 μg/mL, but with no limitations thereto.

In an embodiment of the present disclosure, the composition further comprises a nucleic acid sequence encoding at least one protein selected from the group consisting of OCT4, SOX2, c-Myc, and KLF4. When transduced into somatic cells, the proteins can function as reprogramming factors to induce dedifferentiation of the somatic cells into induced pluripotent stem cells.

In an embodiment of the present disclosure, the somatic cells may be selected from the group consisting of human umbilical vein endothelial cells (HUVEC), human dermal fibroblasts (HDF), human placenta-derived cells (HPC), and a combination thereof.

In an embodiment of the present disclosure, the placenta-derived cells may be placenta-derived fibroblast-like cells that are derived and cultured from the human chorionic plate.

In an embodiment of the present disclosure, the composition may further include an activator of CXCR2, wherein the activator is a ligand for CXCR2. The CXCR2 ligand may be at least one selected from group consisting of GRO-α, GRO-β, GRO-γ, GCP-2, NAP-2, ENA-78, and IL-8 and may be, for example, GRO-α or IL-8, but with no limitations thereto.

In an embodiment of the present disclosure, the composition may further include a human placenta-derived cell conditioned medium (PCCM).

As used herein, the term "human placenta-derived cell conditioned medium" refers to a medium that is prepared by seeding placenta-derived cells onto a gelatin-coated well plate, adding a cell culture medium thereto, incubating the cells, and then collecting the culture medium. The efficacy of placenta-derived feeder cells has been arising as they are identified to be useful for maintaining an undifferentiated state of human embryonic stem cells.

In detail, the PCCM medium may be provided by conducting a placenta-derived cell culturing step of culturing human placenta-derived cells in a cell growth medium supplemented with a culture broth; and the culture broth recovery step of recovering the culture broth. The culture broth may be DMEM (Dulbecco's modified Eagle's medium)/F-12 and may further contain a serum replacement. The PCCM medium may contain a CXCR2 ligand.

Another aspect of the present disclosure pertains to a method for enhancing reprogramming efficiency from somatic cells to induced pluripotent stem cells, the method comprising:

- a somatic transformation step of transducing a nucleic acid sequence encoding for at least one protein consisting of OCT4, SOX2, c-Myc, and KLF4 into somatic cells; and
- an incubating step of incubating the transformed somatic cells with an mTOR activator.

In an embodiment of the present disclosure, the mTOR activator may be 4,6-di-4-morpholinyl-N-(4-nitrophenyl)-1,3,5-triazin-2-amine or a derivative thereof, but is not limited thereto.

In an embodiment of the present disclosure, the incubating step is carried out after the transformation step.

In an embodiment of the present disclosure, MHY1485 is used at a concentration of 0.1 to 10.0 μg/mL, 0.2 to 10.0 μg/mL, 0.5 to 10.0 μg/mL, 0.8 to 10.0 μg/mL, 0.1 to 5.0 μg/mL, 0.2 to 5.0 μg/mL, 0.5 to 5.0 μg/mL, 0.8 to 5.0 μg/mL, 0.1 to 5.0 μg/mL, 0.2 to 5.0 μg/mL, 0.5 to 5.0 μg/mL, 0.8 to 5.0 μg/mL, 0.8 to 3.0 μg/mL, 0.1 to 3.0 μg/mL, 0.2 to 3.0 μg/mL, 0.5 to 3.0 μg/mL, or 0.8 to 3.0 μg/mL, for example, 1.0 to 3.0 μg/mL, but with no limitations thereto.

In an embodiment of the present disclosure, the somatic cells are selected from the group consisting of human umbilical vein endothelial cells, human fibroblasts, human placenta-derived cells, and a combination thereof.

In an embodiment of the present disclosure, the placenta-derived cells may be placenta-derived fibroblast-like cells that are derived and cultured from the human chorionic plate.

In an embodiment of the present disclosure, the incubating step may be carried out in the presence of the CXCR2 activator. The activator may be a ligand. The CXCR2 ligand may be at least one selected from the group consisting of GRO-α, GRO-β, GRO-γ, GCP-2, NAP-2, ENA-78, and IL-8 and may be, for example, GRO-α or IL-8, with no limitations thereto.

In an embodiment of the present disclosure, the incubating step may be carried out in a human placenta-derived cell conditioned medium.

In an embodiment of the present disclosure, the method for enhancing reprogramming efficiency may further comprise a stem cell isolation step of isolating stem cells from a colony formed in the somatic cell incubating step.

According to an embodiment of the present disclosure, incubation with the mTOR activator (MHY1485) subsequent to the transduction of a reprogramming factor into somatic cells may bring about an increase in reprogramming efficiency from somatic cells to induced pluripotent stem cells. Particularly, when the mTOR activator is used along with the PCCM medium, the highest effect of enhancing reprogramming efficiency was obtained.

Advantageous Effects of Invention

The present disclosure is concerned with a composition comprising an mTOR activator for enhancing reprogramming efficiency from somatic cells to induced pluripotent stem cells, and a method for enhancing reprogramming efficiency, using same. In the method, reprogramming factors including OCT4, SOX2, c-Myc, and KLF4 are transduced into somatic cells, followed by incubation with an mTOR activator, thereby remarkably increasing the efficiency of reprogramming to induced pluripotent stem cells. Therefore, the composition and the method can be effectively used for reprogramming from somatic cells to induced pluripotent stem cells.

DETAILED DESCRIPTION

A better understanding of the present disclosure may be obtained through the following examples, which are set forth to illustrate, but are not to be construed to limit the present disclosure.

Throughout the description, the term "%" used to express the concentration of a specific material, unless otherwise particularly stated, refers to (wt/wt) % for solid/solid, (wt/vol) % for solid/liquid, and (vol/vol) % for liquid/liquid.

Figure 1A:
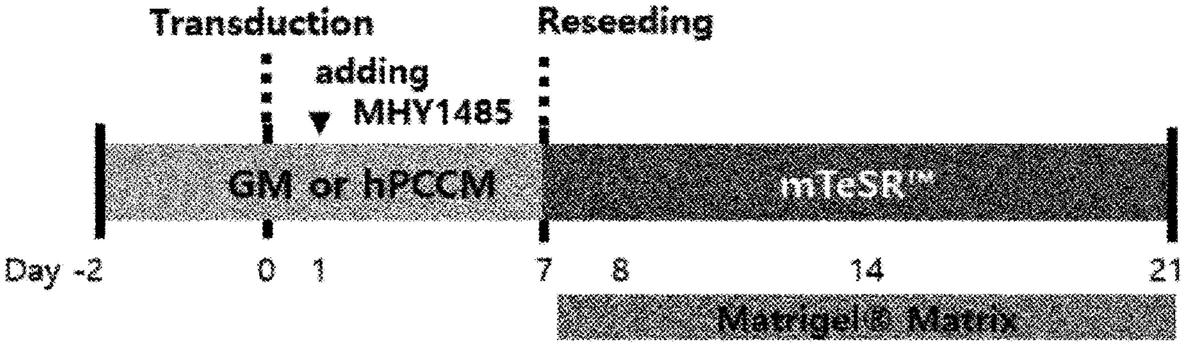
FIG. 1*a* is a scheme illustrating a procedure of transducing reprogramming factors into somatic cells and incubating the somatic cells with 4,6-di-4-morpholinyl-N-(4-nitrophenyl)-1,3,5-triazin-2-amine.

Example 1: Assay for Ability of MHY1485 to Increase Reprogramming Efficiency In order to examine whether 4,6-di-4-morpholinyl-N-(4-nitrophenyl)-1,3,5-triazin-2-amine (MHY1485, CAS Number 326914-06-1), which is an mTOR (mammalian target of rapamycin) activator, has an influence on reprogramming efficiency, reprogramming factors (OCT4, SOX2, c-Myc, KLF4; OSKM) were transduced into primary umbilical vein endothelial cells (HUVEC, ATCC #PCS-100-010), primary human dermal fibroblasts (HDF, ATCC #PCS-201-012), and human placenta derived cells (HPC) via the Sendai virus (SeV) system as shown in FIG. 1*a*.

Twenty-four hours after transduction, the cells were cultured for one week in a placenta-derived cell conditioned medium (PCCM) or growth medium (GM). MHY1485 was added at a dose of 2 μg/mL once per 24 hours for three weeks. After one week of the culturing in a placenta-derived cell conditioned medium (PCCM) or growth medium (GM), the cells were induced to undergo reprogramming for two weeks in Matrigel-coated culture dishes containing mTeSR medium together with MHY1485 under a general pluripotent stem cell culturing condition.

Western blotting identified the expression of CXCR2, mTOR, and cMYC. Autophagic flux activity was identified by staining with Tra-60 specific for stem cell markers.

Figure 1B:
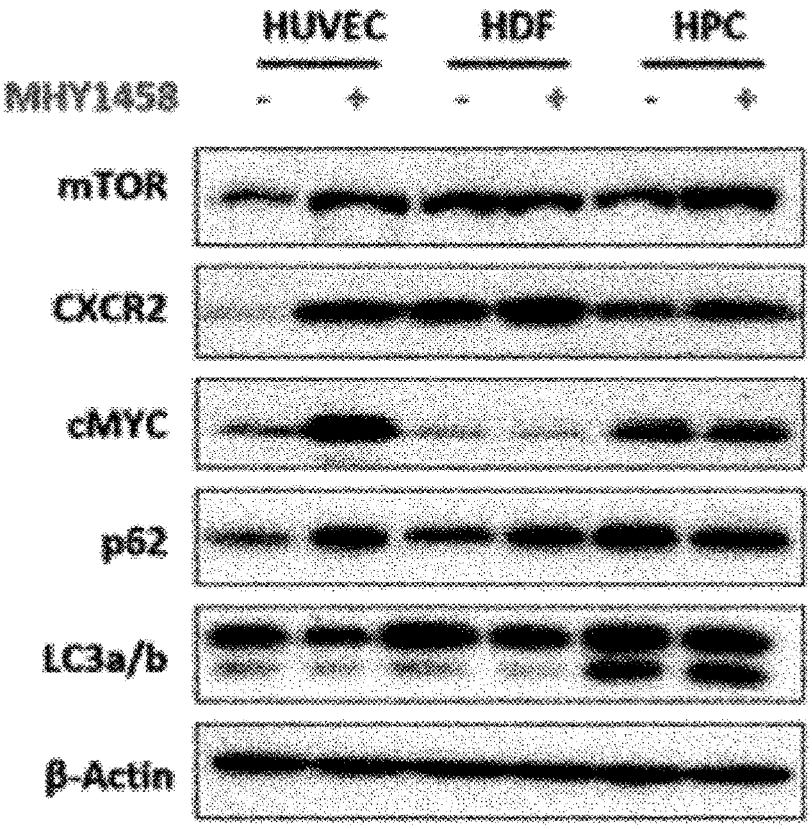
FIG. 1*b* shows western blot analysis results illustrating protein expression levels in primary umbilical vein endothelial cells (HUVEC), primary human dermal fibroblasts (HDF), and human placenta derived cells (HPC) according to the presence or absence of MHY1485.

As can be seen in FIG. 1*b*, treatment with MHY1485 increased the expression of CXCR2, mTOR, and cMYC in somatic cells, but decreased the expression of LC3a/b. An increased expression level of p62 indicated inactivation of autophagic flux.

Figure 1C:
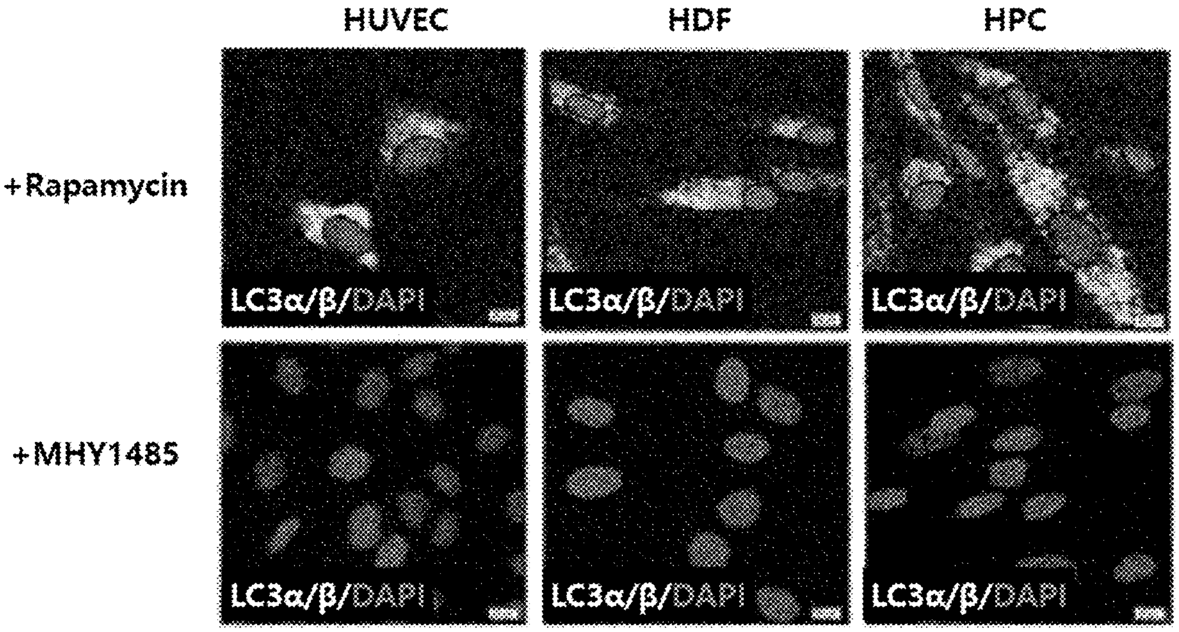
FIG. 1*c* shows immunofluorescence assay images of HUVEC, HDF, and HPC cells demonstrating that treatment with MHY1485 inhibits autophagy.

In an immunofluorescence assay, treatment with MHY1485 decreased the expression of LC3a/b in somatic cells, thus demonstrating the inhibition of autophagy, with the mTOR inhibitor rapamycin serving as a control, as shown in FIG. 1*c*.

Figure 2A:
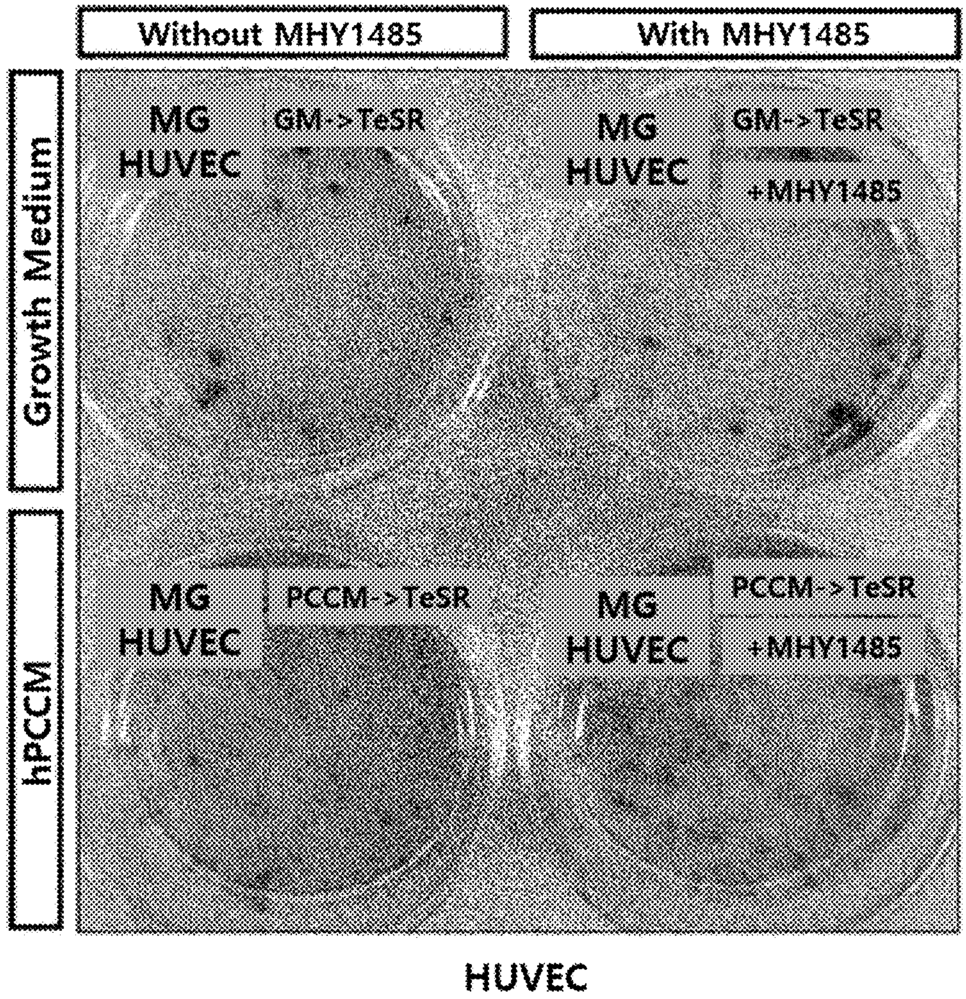
FIG. 2*a* shows images comparing differences in reprogramming efficiency of HUVEC cells between treatment with and without MHY1485 and between placenta derived cell conditioned medium (PCCM) and growth medium.
Figure 2B:
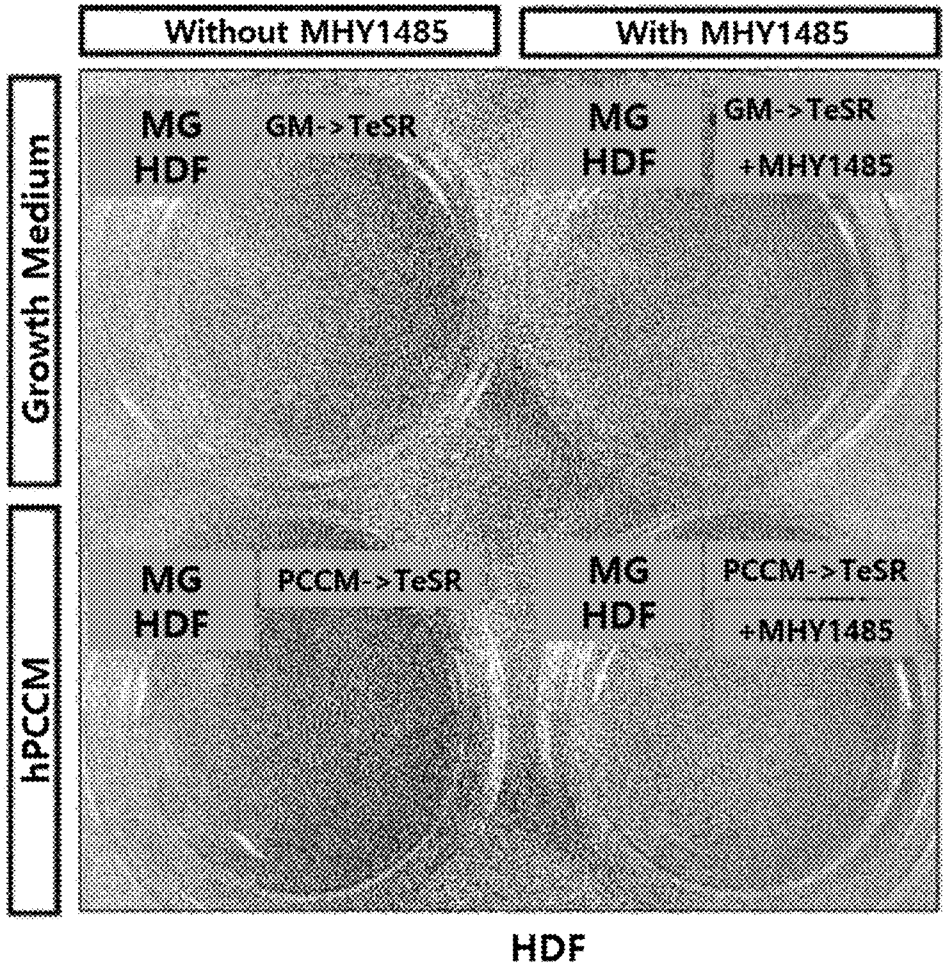
FIG. 2*b* shows images comparing differences in reprogramming efficiency of HDF cells between treatment with and without MHY1485 and between placenta-derived cell conditioned medium (PCCM) and growth medium.
Figure 2C:
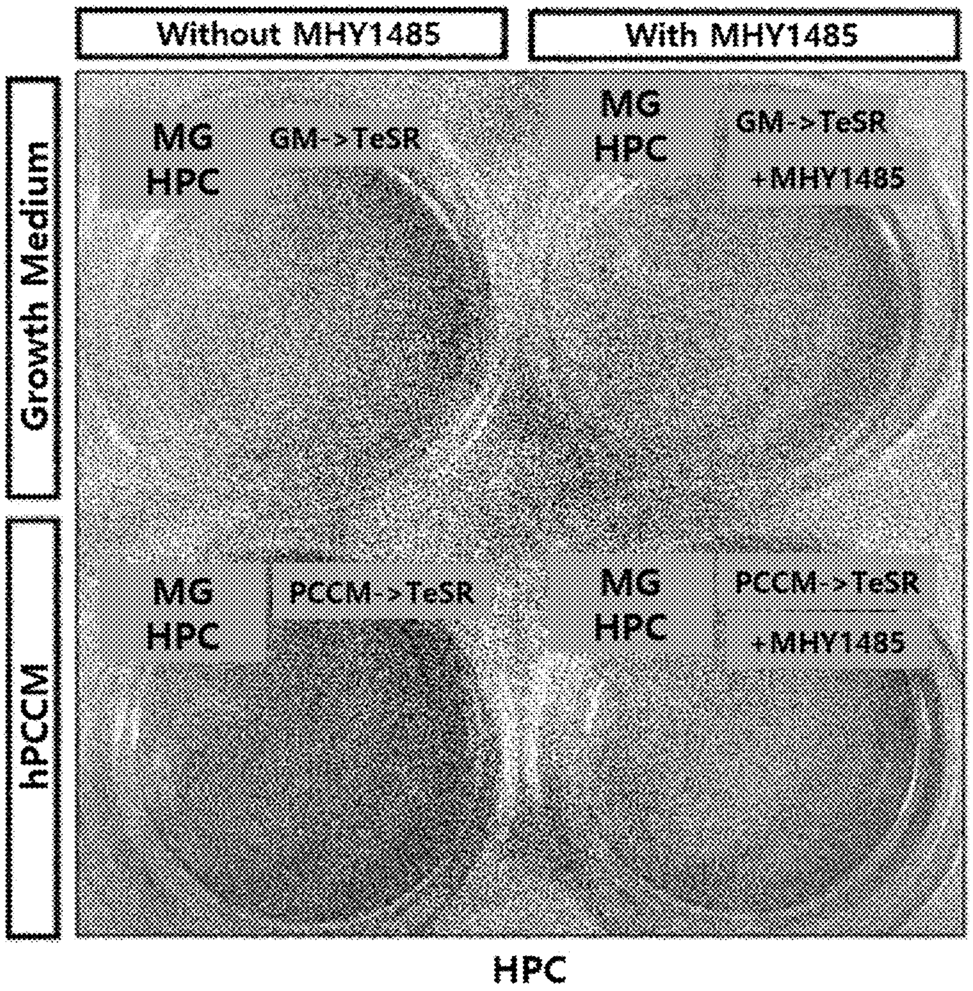
FIG. 2*c* shows images comparing differences in reprogramming efficiency of HPC cells between treatment with and without MHY1485 and between placenta-derived cell conditioned medium (PCCM) and growth medium.

Example 2: Relationship of MHY1485 and CXCR2 Stimuli in Effect of Enhancing Reprogramming Efficiency As shown in FIGS. 2*a* to 2*c*, reprogramming efficiency was increased in all the cells treated with MHY1485, compared to untreated cells. In addition, higher reprogramming efficiency was observed in PCCM than GM.

Therefore, treatment with MHY1485 was found to inactivate autophagy, leading to an increase in reprogramming efficiency.

Figure 3:
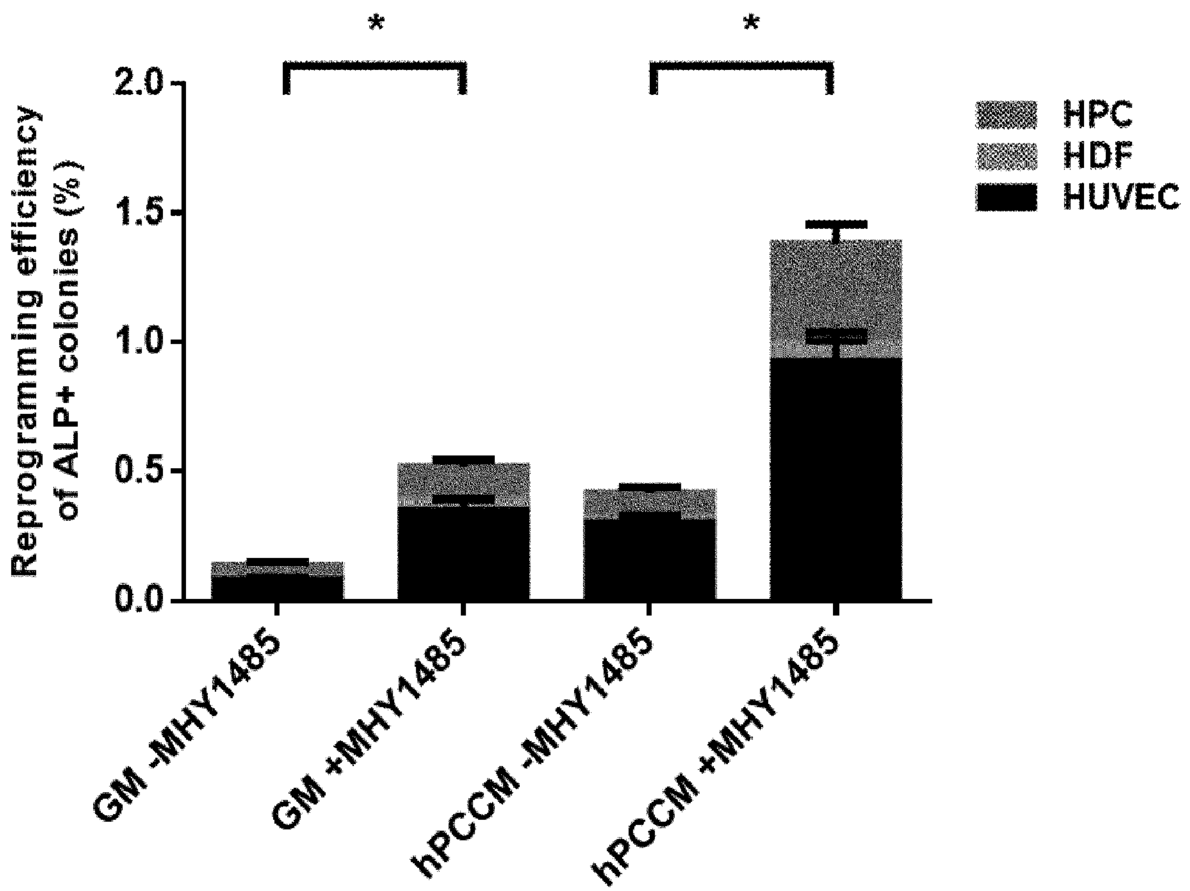
FIG. 3 is a graph comparing differences in reprogramming efficiency of HUVEC, HDF, and HPC cells between treatment with and without MHY1485 and between placenta-derived cell conditioned medium (PCCM) and growth medium.

As is understood from FIG. 3 and Table 1, significantly higher reprogramming efficiency was detected from MHY1485-treated groups than untreated groups.

TABLE 1

| | Reprogramming efficiency (%) | | | |
|---|---|---|---|---|
| | GM MHY1485 | GM + MHY1485 | hPCCM − MHY1485 | hPCCM + MHY1485 |
| HPC | 0.08 | 0.35 | 0.30 | 0.92 |
| HDF | 0.01 | 0.04 | 0.02 | 0.07 |
| HUVEC | 0.05 | 0.13 | 0.10 | 0.39 |

Figure 4:
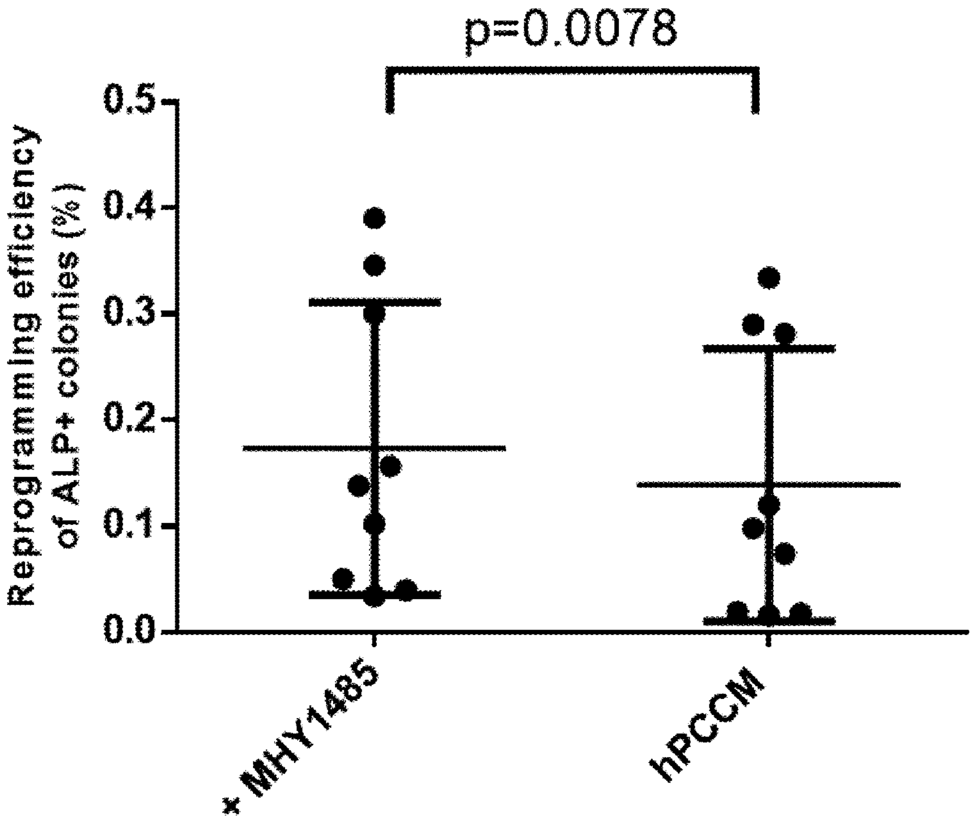
FIG. 4 is a plot comparing differences in reprogramming efficiency of HUVEC, HDF, and HPC cells between treatment with MHY1485 and employment of PCCM.

HUVEC, HDF, and HPC cells were induced to undergo reprogramming by treatment with MHY1485 or in PCCM in three dishes for each cell line. Comparison of a total of 9 dishes therebetween exhibited a significantly high reprogramming efficiency in the MHY1485-treated groups, as shown in FIG. 4 and Table 2.

TABLE 2

| | GM + MHY1485 | hPCCM − MHY1485 |
|---|---|---|
| Reprogramming efficiency (%) | 0.17 | 0.14 |

Therefore, the data obtained above indicate that treatment with MHY1485 brings about a significantly higher effect of increasing reprogramming efficiency, compared to the employment of PCCM medium.

What is claimed is:

1. A method for enhancing reprogramming efficiency from somatic cells to induced pluripotent stem cells, the method comprising:

a somatic transformation step of transducing one or more nucleic acid molecules encoding for all of octamer-binding transcription factor 4 (OCT4), sex determining region Y-box 2 (SOX2), cellular myelocytomatosis oncogene (c-Myc), and Kruppel-like factor 4 (KLF4) into somatic cells; and an incubating step of incubating the transformed somatic cells in a culture medium comprising 4,6-di-4-morpholinyl-N-(4-nitrophenyl)-1,3,5-triazin-2-amine (MHY1485) and a placenta-derived cell conditioned medium (PCCM).

2. The method of claim 1, wherein the somatic cells are at least one selected from the group consisting of human umbilical vein endothelial cells (HUVEC), human dermal fibroblasts (HDF), and human placenta derived cells (HPC).

3. The method of claim 1, wherein the culture medium further comprising a C-X-C motif chemokine receptor 2 (CXCR2) activator.

4. The method of claim 1, further comprising a cell isolation step of isolating induced pluripotent stem cells from a colony formed in the incubating step.

* * * * *